United States Patent
Patel et al.

(10) Patent No.: US 10,323,259 B2
(45) Date of Patent: Jun. 18, 2019

(54) FORMULATION AND PROCESS FOR BIOHYDROGEN PRODUCTION

(71) Applicants: Indian Oil Corporation Limited, Mumbai (IN); Department of Biotechnology, New Delhi (IN)

(72) Inventors: Anil Kumar Patel, Faridabad (IN); Anshu Shankar Mathur, Faridabad (IN); Ravi Prakash Gupta, Faridabad (IN); Deepak Kumar Tuli, Faridabad (IN)

(73) Assignees: Indian Oil Corporation Limited (IN); Department of Biotechnology (IN)

( * ) Notice: Subject to any disclaimer, the term of this patent is extended or adjusted under 35 U.S.C. 154(b) by 9 days.

(21) Appl. No.: 15/426,815

(22) Filed: Feb. 7, 2017

(65) Prior Publication Data

US 2017/0226536 A1    Aug. 10, 2017

(30) Foreign Application Priority Data

Feb. 8, 2016    (IN) .............................. 201621004477

(51) Int. Cl.
C12P 3/00 (2006.01)
C12N 1/20 (2006.01)
C12R 1/145 (2006.01)

(52) U.S. Cl.
CPC .................. *C12P 3/00* (2013.01); *C12N 1/20* (2013.01); *C12R 1/145* (2013.01)

(58) Field of Classification Search
CPC .............. C12R 1/145; C12N 1/20; C12P 3/00
See application file for complete search history.

(56) References Cited

U.S. PATENT DOCUMENTS

| | | | |
|---|---|---|---|
| 7,232,669 B1 | 6/2007 | Lin et al. | |
| 7,816,109 B2 | 10/2010 | Yukawa et al. | |
| 8,211,681 B2 | 7/2012 | Zhang et al. | |
| 8,343,749 B2 | 1/2013 | Nirmalakhandan et al. | |

OTHER PUBLICATIONS

Patel et al. Biohydrogen production from a novel alkalophilic isolate *Clostridium* sp. IODB-O3. Bioresource Technology 175 (2015) 291-297 (Year: 2015).*
R. E. Hungate, "A Roll Tube Method for Cultivation of Strict Anaerobes", vol. 33, 1969, pp. 117-132.
Mei-Ling Chong, et al., "Biohydrogen Production by *Clostridium butyricum* EB6 from Palm Oil Mill Effluent", International Journal of Hydrogen Energy, vol. 34, www.sciencedirect.com; 2009; pp. 164-771.
D. B. Levin, et al., "Biohydrogen Production: Prospects and Limitations to Practical Application", International Journal of Hydrogen Energy, vol. 29, www.sciencedirect.com; 2004; pp. 173-185.
A. E. Mars, et al., "Biohydrogen Production from Untreated and Hydrolyzed Potato Steam Peels by the Extreme Thermophiles *Caldicellulosiruptor saccharolyticus* and *Thermotoga neapolitana*", International Journal of Hydrogen Energy, vol. 35, www.sciencedirect.com; 2010; pp. 7730-7737.
A. K. Patel, et al., Biohydrogen Production from a Novel Alkalophilic Isolate *Clostridium* sp. IODB-O3, Bioresource Technology, vol. 175; 2015; pp. 291-297.
Chao-Wei Wu, et al., "Fermentative Biohydrogen Production from Lactate and Acetate", Bioresiource Technology, vol. 113, 2012, pp. 30-36.
P. C. Hallenbeck, et al., "Biological Hydrogen Production; Fundamentals and Limiting Processes", International Journal of Hydrogen Energy; vol. 27; 2002; pp. 1185-1193.
J. Woodward, et al., "Biotechnology: Enzymatic Production of Biohydrogen", www.nature.com; Nature, vol. 405, Jun. 29, 2000; pp. 1014-1015.
Singh, et al., "Dark Fermentative Biohydrogen Production by Mesophilic Bacterial Consortia Isolated from Riverbed Sediments", International Journal of Hydrogen Energy; vol. 35, 2010; pp. 10645-10652.
Tae-Hyeong Kim, et al., "Effects of Initial Lactic Acid Concentration, HRTs, and OLRs on Bio-Hydrogen Production from Lactate-Type Fermentation", Bioresource Technology, vol. 103; 2012; pp. 136-141.
Chun-Po Juang, et al., "Evaluation of Bioenergy Recovery Processes Treating Organic Residues from Ethanol Fermentation Process", Bioresource Technology; vol. 102; 2011; pp. 5394-5399.
Leena B. Kamalaskar, et al., "High Biohydrogen Yielding *Clostridium* sp. DMHC-10 Isolated from Sludge of Distillery Waste Treatement Plant", International Journal of Hydrogen Energy, vol. 35; 2010; pp. 10639-10644.
M. Matsumoto, et al., "Journal of Bioscience and Bioengineering", vol. 103, No. 3; 2007; pp. 236-241.
T. de Vrije, et al., "Hydrogen Production from Carrot Pulp by the Extreme Thermophiles *Caldeicellulosiruptor saccharolyticus* and *Thermotoga neapolitana*", International Journal of Hydrogen Energy, vol. 35; 2010; pp. 13206-13213.
T. A. Ngo, et al., "Thermophilic Fermentative Hydrogen Production from Xylose by *Thermotogo neapolitana* DSM 4359", Renewable Energy, vol. 37; 2012; pp. 174-179.
S. A. Munro, et al., "The Fermentation Stoichiometry of *Thermotogo neapolitana* and Influence of Temperature, Oxygen, and pH on Hydrogen Production", Biotech. Progress, Wiley InterScience, www.interscience.wiley.com; vol. 25; Jun. 23, 2009; pp. 1035-1042.
T. Noike, et al., "Inhibition of Hydrogen Fermentation of Organic Wastes by Lactic Acid Bacteria", International Journal of Hydrogen Energy; vol. 27; 2002; pp. 1367-1371.

(Continued)

*Primary Examiner* — Taeyoon Kim
(74) *Attorney, Agent, or Firm* — Blank Rome LLP

(57) ABSTRACT

The present invention relates to a process for enhancing hydrogen production in an anaerobic fermentative hydrogen production process. The present invention also provides a production media, more specifically, a sugar production media for use in an anaerobic fermentative hydrogen production process to enhance hydrogen production. The present invention also provides a novel strain *Clostridium* sp., MTCC 25082 for use in an anaerobic fermentative hydrogen production process for enhancing hydrogen production.

7 Claims, 2 Drawing Sheets

(56) References Cited

OTHER PUBLICATIONS

You-Kwan Oh, et al., "Metabolic-flux Analysis of Hydrogen Production Pathway in *Citrobacter amalonaticus* Y19", International Journal of Hydrogen Energy; vol. 33; 2008; pp. 1471-1482.
B. Baghchehsaraee, et al., "The Effect of Heat Pretreatment Temperature on Fermentative Hydrogen Production Using Mixed Cultures", International Journal of Hydrogen Energy; vol. 33; 2008; pp. 4064-4073.

\* cited by examiner

FORMULATION AND PROCESS FOR BIOHYDROGEN PRODUCTION

FIELD OF THE INVENTION

The present invention relates to a process for enhancing biohydrogen production. The present invention also relates to a production media for enhancing production of biohydrogen. In particular, the present invention relates to a method for enhancing hydrogen production in a process with supplementation of lactic acid, acetic acid and butyric acid in the production media.

BACKGROUND OF THE INVENTION

Previous work on enhancement of hydrogen production via biological process were attempted using molecular technique for the modification of microbial biohydrogen pathway with suppression of lactic and succinic acid biogenic path (Yukawa et al., 2010: U.S. Pat. No. 7,816,109B2) or exploration of organic waste containing $H_2$ producing microbes and an activated carbon based carrier combination to adhere and proliferate more biomass for enhance H2 production (Lin et al., 2007: U.S. Pat. No. 7,232,669 B1) or membrane based two stage biohydrogen production from organic waste using dark and photo-linked fermentation (Nirmalakhandan et al., 2013; U.S. Pat. No. 8,343,749 B2) or exploitation of in vitro enzymatic process in water solution that effectively converts low cost feed-stocks into high yield biohydrogen (Zhang et al., 2012; U.S. Pat. No. 8,211,681 B2) and so on. None of the patent has been filed regarding supplementation of organic acids (lactic, acetic and butyric acids) to inhibit their production via feed-back inhibition or other related mechanism for enhancement of biohydrogen production from glucose or reducing sugars from any organic waste. However, Kim et al., (2012) have been reported lactic acid addition enhanced biohydrogen yield (from 1.41-1.72 mol/mol-Glc) moderately from glucose in continuous fermentation operation. Baghchehsaraee et al. (2009) reported that more hydrogen was produced using a mixed substrate with starch and lactic acid.

Masumoto and Nishimura (2007) and Wu et al., (2012) found that mixed substrate of acetic acid and lactic acid enhanced hydrogen production (without glucose). However these processes have utilized higher lactic acid concentration compares to current study and glucose was lacking in studies of Masumoto and Nishimura (2007) and Wu et al., (2012). Moreover these processes were lacking the addition of acetic and butyric acids along with lactic acid hence processes were not turned into significant enhancement in biohydrogen production. Combination of acetic and butyric acid with lactic acid was important which has resulted into significant enhancement of biohydrogen yield (max 4.5 mol/mol-Glc) from glucose in the current study.

OBJECTIVE OF THE INVENTION

It is the primary objective of the invention to provide a method for enhancing biohydrogen production.

It is another objective of the invention to provide a production media for enhancing biohydrogen production.

It is still another objective of the invention to provide a strain of Clostridium sp., MTCC 25082 (Clostridium sp. IODB-O3), for enhancing biohydrogen production.

It is further objective of the present invention to provide a process for significant improvement in hydrogen production in a process, with supplementation of lactic acid, acetic acid and butyric acid in production media, by using an anaerobic microorganism, Clostridium sp. IODB-O3.

It is further objective of the present invention to provide a process for significant improvement in hydrogen production, whereby after completion of fermentation, the culture broth is recycled to get water, acetic acid and butyric acid fractions, and reuse them in the fermentation to economize the process.

It is a further objective of the present invention to provide a process for significant improvement in hydrogen production, whereby the installation and operational costs are reduced.

SUMMARY OF THE INVENTION

In one aspect, the present invention provides a process for enhancing hydrogen production in an anaerobic fermentative hydrogen production process. The said process comprises:
  providing a production media,
  incubating the production media with an anaerobic Clostridium sp. for anaerobic fermentative reaction to produce hydrogen,
  wherein the process comprises supplementing the production media with lactic acid, acetic acid and butyric acid.

In one embodiment, the production media used in the process is sugar based production media. The sugar used in the production media is selected from glucose, lactose, xylose, Wheat Straw Pre-hydrolysate (WSPH), Wheat Straw Enzymatic-hydrolysate (WSEH). The source of said sugars is selected from lignocellulosic biomass prehydrolysate and enzymatic hydrolysate and whey waste. The source of lactic acid is cheese whey. The source of acetic acid is distillery waste. The acetic acid and butyric acid is also produced from the culture during anaerobic fermentation of sugar in defined fermentative condition.

In another embodiment, the Clostridium sp. used in the process of the present invention is Clostridium sp., MTCC 25082.

In preferred embodiments, the process of the present invention employs specific amounts of lactic acid, acetic acid and butyric acid, whereby the production of hydrogen is enhanced. In a specific embodiment, the production media used in the process of the present invention employs lactic acid in an amount of 0.2-0.5% w/v, acetic acid in an amount of 1.5-2.5% w/v, and butyric acid in an amount of 0.2-0.5% w/v. In a most preferable embodiment, the amount of lactic acid in the production media is about 0.3% w/v, the amount of acetic acid is about 2% w/v, and the amount of butyric acid is about 0.5% w/v. In a preferred embodiment, the ratio of acetic acid and butyric acid in the production media, before the fermentation step is 4:1. In a further preferred embodiment, the present invention provides a process, wherein the acetic acid and butyric acid fractions and even water are recovered from the fermentation culture broth and are recycled in the process.

The process of the present invention enhances the hydrogen production, wherein the amount of hydrogen produced is 3.5 to 4.5 mol/mol-sugar. Without being bound by the theory, it is assumed that the hydrogen production is similar for all sugars, with slight variation; however, combination of acid fractions is playing crucial role in metabolic augmentation of hydrogen production.

The present invention also provides a production media for enhancing hydrogen production in an anaerobic fermentative hydrogen production process. The production media comprises of: $K_2HPO_4$ in an amount of 400 to 500 mg/L;

$KH_2PO_4$ in an amount of 400 to 500 mg/L; $(NH_4)_2SO_4$ in an amount of 800 to 1000 mg/L; NaCl in an amount of 800 to 1000 mg/L; $MgSO_4.7H_2O$ in an amount of 80 to 100 mg/L; $CaCl_2$ in an amount of 80 to 100 mg/L; Hemine in an amount of 0.0004 to 0.0006 mg/L; $Na_2CO_3$ in an amount of 3000 to 5000 mg/L; L-Cysteine.HCl in an amount of 400 to 600 mg/L; Resazurin in an amount of 0.5 to 0.7 mg/L; Biotin in an amount of $4.0\times10^{-2}$ to $6.0\times10^{-2}$ mg/L; p-Amino benzoic acid in an amount of $1.0\times10^{-2}$ to $2.0\times10^{-2}$ mg/L; trace elements; $MnSO_4.H_2O$— $2.0\times10^{-3}$ to $4.0\times10^{-3}$; $FeSO_4.6H_2O$— $6.0\times10^{-3}$ to $9.0\times10^{-3}$ and $CoCl_2.6H_2O$— $2.0\times10^{-3}$ to $4.0\times10^{-3}$. Lactic acid in an amount of 0.2-0.5% w/v; acetic acid in an amount of 1.5-2.5% w/v; butyric acid in an amount of 0.2-0.5% w/v; sugar in an amount of 8000 to 10000 w/v; and water. The sugar used in the production media is selected from glucose, lactose, xylose, WSPH and WSEH.

The source of said sugars is selected from lignocellulosic biomass prehydrolysate, enzymatic hydrolysate and cheese whey waste. The source of lactic acid was cheese whey, acetic acid was distillery waste, butyric acid supplementation is initially needed and acetic and butyric acid was mainly produced from culture during anaerobic fermentation of sugar in defined fermentative condition.

In a preferred embodiment, the present invention provides a production media comprising: $K_2HPO_4$ in an amount of 450 mg/L; $KH_2PO_4$ in an amount of 450 mg/L; $(NH_4)_2SO_4$ in an amount of 900 mg/L; NaCl in an amount of 900 mg/L; $MgSO_4.7H_2O$ in an amount of 90 mg/L; $CaCl_2$ in an amount of 90 mg/L; Hemine in an amount of 0.00049 mg/L; $Na_2CO_3$ in an amount of 4000 mg/L; L-Cysteine.HCl in an amount of 500 mg/L; Resazurin in an amount of 0.6 mg/L; Biotin in an amount of $4.0\times10^{-2}$ mg/L; p-Amino benzoic acid in an amount of $1.0\times10^{-2}$ mg/L; $MnSO_4.H_2O$ in an amount of $3.0\times10^{-3}$ mg/L; $FeSO_4.6H_2O$ in an amount of $8.0\times10^{-3}$ mg/L; $CoCl_2.6H_2O$ in an amount of $3.0\times10^{-3}$ mg/L; lactic acid in an amount of 0.3% w/v; acetic acid in an amount of 2% w/v; butyric acid in an amount of 0.5% w/v; glucose in an amount of 1% w/v; and water.

DETAILED DESCRIPTION OF THE INVENTION

Figure 1:
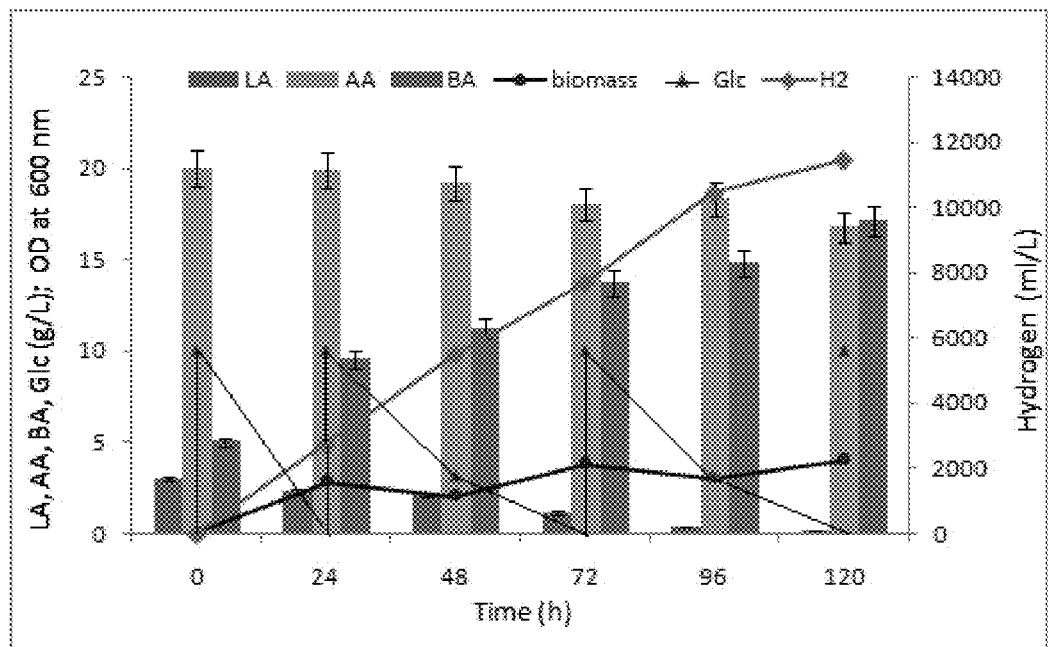
FIG. 1 describes the effect of lactic acid (LA) on $H_2$ production in the production media by *Clostridium* sp. IODB-O3 containing 4:1 initial ratio of acetic acid (AA) and butyric acid (BA).

While the invention is susceptible to various modifications and/or alternative processes and/or compositions, specific embodiment thereof has been shown by way of example, including the drawings and tables and will be described in detail below. It should be understood, however that it is not intended to limit the invention to the particular processes and/or compositions disclosed, but on the contrary, the invention is to cover all modifications, equivalents, and alternatives falling within the spirit and the scope of the invention as defined by the appended claims.

The tables and protocols have been represented where appropriate by conventional representations, showing only those specific details that are pertinent to understanding the embodiments of the present invention so as not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

In one embodiment, the present invention discloses a formulation of production media for production of biohydrogen/hydrogen. The invention also discloses a process for the production of biohydrogen using the production media as described herein.

The invention also discloses a process for enhancing hydrogen production in an anaerobic fermentative hydrogen production process using the production media of the present invention. Anaerobic fermentative hydrogen production process is a cost effective biological process for production of hydrogen or biohydrogen. Such process accomplishes waste reduction, energy generation and support sustainability as well as the economic viability of the process. Anaerobic fermentative hydrogen production process is a fermentative conversion of organic substrate to biohydrogen. Complex organic compounds such as carbohydrates and proteins are converted into biohydrogen, volatile fatty acids (VFAs) and $CO_2$ by fermentative bacteria at ambient temperature and in absence of light, which saves lot of energy. It is a complex process manifested by diverse groups of bacteria, involving a series of biochemical reactions using three steps similar to anaerobic conversion (Hydrolysis, fermentation and acetogenesis). Such fermentation differs from photofermentation in that it proceeds without the presence of light. Fermentative/hydrolytic microorganisms hydrolyze complex organic polymers to monomers, which are further converted to a mixture of lower-molecular-weight organic acids and alcohols by obligatory producing acidogenic bacteria.

In accordance with the present invention, a production media conducive to the growth of microorganisms exhibiting NADPH mediated $H_2$ evolution is provided for enhanced evolution of $H_2$ by such microorganisms. The production media is supplemented with certain concentrations of lactic, acetic and butyric acid contributing to enhanced biohydrogen yield by inhibiting key enzymes viz. lactate dehydrogenase, phosphotransacetylase and acetate kinase in the EMP pathway for lactic and acetic acid production or related unknown mechanism.

The production media is subjected to a reduction process under pure $N_2$ purging with mild heating, acclimation, treatment with a reducing agent and a pH controlling solution, and combinations thereof, in order to allow the hydrogen-producing anaerobic bacteria to grow anaerobically. The media color turns from pink to colorless, was sterilized at 121° C. and 15 lb pressure for 15 min after setting the pH 8.5.

In accordance with the present invention, a biohydrogen production media was provided comprising of (mg/L):

$K_2HPO_4$—450; $KH_2PO_4$—450; $(NH_4)_2SO_4$—900; NaCl—900; $MgSO_4.7H_2O$—90; $CaCl_2$—90; Hemine—0.00049; $Na_2CO_3$—4000; L-Cysteine.HCl—500 (reducing agent); Resazurin—0.6 (redox indicator); Vitamins: biotin—$4.0 \times 10^{-2}$ and p-Amino benzoic acid—$1.0 \times 10^{-2}$ and trace elements: $MnSO_4.H_2O$—$3.0 \times 10^{-3}$; $FeSO_4.6H_2O$—$8.0 \times 10^{-3}$ and $CoCl_2.6H_2O$—$3.0 \times 10^{-3}$. The biohydrogen production media also contains acetic acid 2% w/v, butyric acid 0.5% w/v, lactic acid 0.3% w/v and glucose 1% w/v, which are one of the best ratio in terms of biohydrogen yield. In an embodiment of the present invention, acetic acid, butyric acid and lactic acid are present in certain optimized concentrations. However, in yet another embodiment, acetic acid is present in 1.5-2.5% (w/v), butyric acid is present in the range of 0.2-0.5% (w/v), lactic acid is present in the range of 0.2-0.5% (w/v), and lactose is present in the range of 0.5-1.0% (w/v). In yet another embodiment, after the completion of fermentation the culture broth can be recycled to get water, acetic acid and butyric acid fractions back to reuse them to economize the process.

For biohydrogen production process, three organic acids are required in the range given in Table 1. However, for economic viability, acetic acid containing industrial effluent and whey waste is used as feedstock (after blending) in the proportion to reach given range to start the process. The resulting mixed waste stream would comprise of lactose sugar, acetic and lactic acid for biohydrogen production in optimum range. Moreover, only 0.2-0.5% butyric acid will be required initially to begin the experiment. Thereafter, the microbe employed in the process would produce it during the fermentation and external addition of butyric acid would not be required in further stages of fermentation.

TABLE 1

Organic fractions, their working range and supply source for biohydrogen production process

| Sl. No. | Name of acid | concentration range works | Supply source | Commercial Price (Rs/L) |
|---|---|---|---|---|
| 1 | Acetic acid | 1.5-2.5% | distillation industry effluent or culture broth of gas fermentation | none |
| 2 | Butyric acid | 0.2-0.5% | initially to be added externally | ≈1020 |
| 3 | Lactic acid | 0.2-0.5% | whey waste | none |
| 4 | Lactose | 0.5-1.0% | whey waste | none |

Without being bound by theory, it is expected that, Lactose is broken into glucose and galactose units and utilized by employed microorganism for biohydrogen production, which does not require any pre-treatment process. Approx. 400 L whey is required for 10000 L hydrogen production; Calorific value of hydrogen is approx. 3 times more than hydrocarbon fuels.

For biohydrogen process, waste culture broth of gas fermentation is supported to attain 1.5-2.5% acetic acid range and is mixed with whey waste to get lactose (0.5-1.0%) and lactic acid (0.2-0.5%) fractions to start fermentation in continuous or fed batch mode. Externally 0.2-0.5% butyric acid is needed to begin the process and once the cell biomass attains 0.2-0.3% concentration, butyric acid is produced in the required quantity by microbes itself for the rest of the process.

An aspect of the present invention discloses the process of generating biohydrogen with the use of the production media described herein. In accordance with the present invention, the strain *Clostridium* sp. IODB-O3 accession no. [MTCC 25082] deposited on Jan. 11, 2016 at Microbial Type Culture Collection and Gene Bank, Institute of Microbial Technology, Shanti Path, 39A, Sector 39, Chandigarh, 160036 was used for generating biohydrogen. The bacterial strain employed in this study is pure isolate obtained from sample collected from a local wastewater pre-treatment plant—Okhla Sewage Treatment Plant at Okhla (latitude: 28° 33' 13.69" N, longitude: 77° 16' 54.18" E), in New Delhi, India. Purification of this consortium was done using Hungate culture technique (Hungate, R. E, 1969) and best purified single isolate was selected on the basis of maximum $H_2$ production for this study and was designated as IODB-O3. The strain *Clostridium* sp. IODB-O3 is gram positive, rod-shaped, obligate anaerobic fermentative bacilli which showed optimal growth at temperature 37° C. This isolate can grow in wide pH range between 5.5-10.5, however better growth was observed at pH 8.5. A 16S rDNA gene analysis revealed its 98% similarity with *Clostridium* sp. Nucleotide sequence of *Clostridium* sp. IODBO3 isolate has been submitted to the NCBI gene bank under accession number of KM213015.

In accordance with the present invention, the process for generating biohydrogen can be carried out in batch, fed-batch and continuous mode. The size of inoculum used was 5% (v/v) in sterilized production media, which is defined above. In an embodiment, production of biohydrogen is carried out while supplying glucose as carbon source in the concentration of 10 g/L in fed batch mode intermittently after depletion every 48 h or more. Organic acids were not re-added with glucose (except lactic acid after 96 h). The temperature was maintained at 37° C. and pH was maintained at 8-8.5 with addition of 1M KOH, which facilitated carbon utilization under optimum fermentation condition. Incubation time was 24 hrs with agitation at 120 rpm. The gas pressure was released to reduce negative effect of $H_2$ pressure in the headspace at every 24 h and pH was re-maintained at 8.5.

Having described the basic aspects of the present invention, the following non-limiting examples illustrate specific embodiment thereof.

EXPERIMENTAL

A. The general composition of biohydrogen minimal (BM) media (production media) is given in Table 2. The BM media was implemented in the study after certain modification with supplementation of 3, 2.5, and 5 g/L lactic, acetic and butyric acid concentration respectively. All the chemicals used in the experiment were procured from Himedia. The components of the production media are added stepwise. Firstly, all the salts were added followed by vitamins, trace elements, resazurin and glucose and/or cheese whey added as substrate. The concentration of 8-10 g/L glucose/lactose was used in the media. The minimal medium was set to pH 8.5 with 1 N HCl and 1 N NaOH solution. L-Cysteine was added in pre-warmed media in order to remove the oxygen under $N_2$ purging. The media then turned from pink to colourless. The bottles were then sealed with butyl rubber stopper and aluminium cap using crimper. Sealed bottles with media were autoclaved for 15 min at 121° C. and 15 psi pressure.

TABLE 2

General composition of biohydrogen production minimal media

| Components | Concentration (mg/L): |
|---|---|
| Minerals | |
| $K_2HPO_4$ | 450 |
| $KH_2PO_4$ | 450 |
| $(NH_4)_2SO_4$ | 900 |
| NaCl | 900 |
| $MgSO_4 \cdot H_2O$ | 90 |
| $CaCl_2$ | 90 |
| Hemin | 0.00049 |
| Substrate & supplements | |
| Glucose | 10000 |
| Yeast extract | 3000 |
| Vitamins: | |
| biotin | $4.0 \times 10^{-2}$ |
| p-Amino benzoic acid | $1.0 \times 10^{-2}$ |
| Trace elements: | |
| $MnSO_4 \cdot H_2O$ | $3.0 \times 10^{-3}$ |
| $FeSO_4 \cdot 6H_2O$ | $8.0 \times 10^{-3}$ |
| $CoCl_2 \cdot 6H_2O$ | $3.0 \times 10^{-3}$ |
| L-Cystein•HCl (reducing agent) | 500 |
| Resazurin (redox indicator) | 0.6 |
| $Na_2CO_3$ | 4000 |

To examine the effect of lactic acid with given concentrations of acetic acid and butyric acid on biohydrogen yield, different sets of experiments were carried out. Glucose concentration was 10 g/L in each set of experiment. The concentration of lactic acid used was 3 g/L (w/v) wherever required. However, varying concentration ranging from 5-20 g/L (w/v) of acetic acid and butyric acid were used. Each set of experiment was carried out in triplicate and the results given here is average of three independent fermentation samples.

B. General Operating Methods and Equipment: Experiments were performed in 100 ml anaerobic serum bottles with working volume of 50 ml in fed-batch operation mode. The sterilized basal medium was inoculated anaerobically with 18 h grown *Clostridium* sp. IODB-O3 culture (inoculum) for biohydrogen production. Inoculated bottles were incubated at 37° C. in a shaker at 120 rpm for 24 h. The liquid and gas samples were taken for analysis of hydrogen, organic acids (acetic, butyric, lactic acid etc.), cell biomass and final pH. The pH was reset at 8.5 and gas pressure was removed from headspace in every 24 h. During fed-batch operation in bottles, fermentation was carried out successfully up to 24 h, thereafter pH drop was observed due to organic acid production. Lower pH also affects utilization of carbon source negatively. Fermentation was able to continue optimally after 24 h by manual pH readjustment in order to utilize carbon source completely. Growth of *Clostridium* sp. IODB-O3 was monitored by determination of the optical density (OD) at 600 nm using UV visible spectrophotometer (UV-2450, Shimadzu, Japan). Initial and final pH was measured by pH meter (Mettler-Toledo, India). Refinery Gas Analyser (RGA) (Agilent 6890N, USA) equipped with thermal conductivity detector (TCD) was used for analysis of gas composition in the bottle's headspace. A stainless steel column packed with molecular sieve (2 m×2 mm ID) (Nucon, India) was used. Nitrogen was used as the carrier gas at the rate of 40 ml/min. The operating temperatures of the oven, inlet port and the detector were 50, 100, and 250° C. respectively. Quantitatively organic acids and reducing sugars were analyzed with HPLC (Waters, USA) equipped with a refractive index detector fitted with an Aminex HPX-87H column 300 mm×7.8 mm ID (Bio-Rad Labs, Hercules, Calif.) operated at 50° C. with 5 mM $H_2SO_4$ as mobile-phase (at a flow rate of 0.6 ml/min) at 220 nm wavelength. GC and HPLC were calibrated by injecting standards of different concentrations. The calibration curve obtained for all the standards showed $R^2$ value close to 0.997 and therefore these methods were accepted as accurate and precise.

Example: 1

The Effect of Lactic Acid Supplementation Along with Acetic Acid and Butyric Acid in the Glucose Biohydrogen Production Media, on Enhancement of Biohydrogen Production This embodiment investigates the effect of lactic acid addition (3 g/L (w/v)) in production media of *Clostridium* sp IODB-O3 for biohydrogen production. The production media mainly consists of glucose as a substrate (10 g/L (w/v)) with all growth components, pH indicator, reducing agents and also supplemented with higher concentration of acetic acid (20 g/L (w/v)) and butyric acid (5 g/L (w/v)) to support lactic acid role as inducer in enhancement of biohydrogen production. The medium pH, incubation temperature, time and agitation were 8.5, 37° C., 48 h, 120 rpm respectively.

I. Preparation of Seeding Culture:

*Clostridium* sp IODB-O3 was obtained from anaerobic sewage sludge from Okhla, Delhi. A 5% (v/v) of 18 h old IODB-O3 culture was used as inoculums for the experiment. Media composition is given in Table 2 and the methods and culture conditions are described in section B above.

II. Anaerobic Fermentative Hydrogen Production Process:

The hydrogen production efficiency of the anaerobic fermentative reaction system operated under a high organic acid concentration and added lactic acid thereto and using glucose as a substrate was investigated. Glucose (concentration: 10 g/L) was periodically fed to the culture after depletion at every 48 h (after biomass generation) of incubation and anaerobic fermentative reaction was allowed to take place in the fed batch mode under the condition given in section B of experimental materials. The analysis of gas and liquid samples after anaerobic fermentative reaction were done for hydrogen, organic acid, biomass concentration and final pH according to the methods described under the preceding section B of experimental. The data are expressed in means of each set of experiment carried out in triplicate and the result given here is average of three independent fermentation samples.

III. Results and Discussion:

Referring to FIG. 1, the hydrogen yield, organic acid, glucose and the biomass concentration were plotted against the incubation hour. Furthermore, higher acetic acid, lower butyric and lactic acid concentrations exhibited enhancement of biohydrogen yield significantly. The biohydrogen yield improved significantly after cell biomass is adequately generated and 1$^{st}$ glucose feed was incorporated in the fermentation. The maximum yield obtained was 4.52 mol-$H_2$/mol-glucose and in subsequent cycle the yield obtained was average 4.0-4.2 mol-$H_2$/mol-glucose. Improvement in $H_2$ yield was measured after cell biomass attained more than 2.5 g/L after 24 h of fermentation. Based on the performance of IODB-O3 strain in presence of lactic acid in this experiment, the biohydrogen yield was improved by maximum 72.4% as compared to normal fermentation condition without lactic acid supplementation in the media.

Referring to FIG. 1, approximately 1.3 g lactic acid (initial 3 g) and 2 g acetic acid were utilized during the fermentation period, offering maximum $H_2$ yield after first fed. The improvement in $H_2$ yield from normal yield range (2.6 mol-$H_2$/mol-glucose) cannot be due to consumed fractions of lactic acid and acetic acid, hence, this explained that it might lead to enhanced mechanism that of the NAD(P)H-ferrodoxin dependent oxidoreductase (NFOR) hydrogenase mediated $H_2$ evolution which is commonly known in Clostridium system in the biohydrogen pathway and that is turning eventually into higher $H_2$ yield using glucose as a feed. Increased initial organic acid concentration does not dissociate in ionic form hence, go across the cell wall and effect internal pH inversely. To avoid non-favorable pH, microbial system generates higher NADH which might be available for hydrogen production. However, the exact mechanism for enhancement of biohydrogen yield in this process cannot be determined. It is the focus of current investigation now. Moreover, acetic acid was slightly utilized by culture until the lactic acid was present. Thereafter acetic acid was not consumed further, and remained in the same level in further fermentation. After 72 h of fermentation, lactic acid was depleted and the system behaves normally. Hence to obtain better $H_2$ yield, lactic acid concentration must be maintained to continue their positive effect in the fermentation. Oh et al., (2008) has suggested that the $H_2$ yield more than 4 mol/mol-glucose is possible if $H_2$ is produced from NAD(P)H by non-native NAD(P)H-linked hydrogenase where NAD(P)H is supplied at a high rate through the PP pathway. Although NAD(P)H is rather positive reductant than ferredoxin and flavodoxin and is known in thermophile, to be used for $H^+$ reduction into $H_2$, however PP pathway is not applicable here in glucose fermentation. Hence deep insights are needed to understand the actual mechanism involved in the fermentation comprising lactic acid with higher acetic acid and lower butyric acid combination which has offered higher $H_2$ yield.

Referring to FIG. 1, the hydrogen yield of the anaerobic fermentative hydrogen production system was significantly decreased in every 24 h gas volume measurement (two step measurement process in 48 h) after the depletion of lactic acid. It was assumed that the presence of added lactic acid along with high acetic acid concentration might have inhibited lactose dehydrogenase and phosphotransacetylase and acetate kinase gene respectively, which might have resulted to utilization of saved carbon source (from acid generation) towards hydrogen generation to complete the fermentation step in the anaerobic hydrogen fermentation, thereby further enhancing the hydrogen yield. The concentration ratio of all three organic acids was very much crucial in these experiments in terms of hydrogen yield.

TABLE 3

Results for FIG. 1

| Time (h) | LA (g/L) | AA (g/L) | BA (g/L) | Cumulative $H_2$ (ml/L) | Glucose (g/L) | Biomass (g/L) |
|---|---|---|---|---|---|---|
| 0 | 3 | 20 | 5 | 0 | 10 | 0.1 |
| 24 | 2.3 | 19.9 | 9.5 | 2750 | 10 | 2.87 |
| 48 | 2.1 | 19.2 | 11.2 | 5500 | 3.2 | 2.11 |
| 72 | 1.15 | 18 | 13.7 | 7700 | 10 | 3.84 |
| 96 | 0.37 | 18.3 | 14.8 | 10450 | 3.1 | 3.06 |
| 120 | 0.15 | 16.8 | 17.1 | 11560 | 10 | 4.04 |

TABLE 3-continued

Approximately 65-70% carbon source was utilised in first 24 h of fermentation and the rest was utilized after pH was reset. After 48 h of fermentation, the carbon source was completely depleted hence 10 g/L (w/v) glucose concentration was re-added, likewise fed-batch operation was continued. However the lag phase was comparatively more with culture comprising lactic acid and fermentation was delayed compared to normal fermentation. Biohydrogen produced during 48 h was measured in two steps. In first step, gas production was equal or more in volume than that of the second step of fermentation after pH adjustment.

Example 2

The Effect of Acetic and Butyric Acids (without Lactic Acid Addition) Supplementation in the Biohydrogen Production Media on Enhancement of Anaerobic Biohydrogen Production This embodiment investigates the effect of no lactic acid addition in production media of Clostridium sp IODB-O3 for the production of biohydrogen. However acetic and butyric acid were used at same concentration as discussed in experiment of example 1. Production media mainly comprised of glucose as a substrate with all growth components, pH indicator, reducing agents and also supplemented with higher concentration of acetic acid (20 g/L (w/v)) and butyric acid (5 g/L w/v) but no lactic acid as inducer for enhancement of biohydrogen production. The medium pH, incubation temperature, time and agitation were 8.5, 37° C., 48 h, 120 rpm, respectively.

Figure 2:
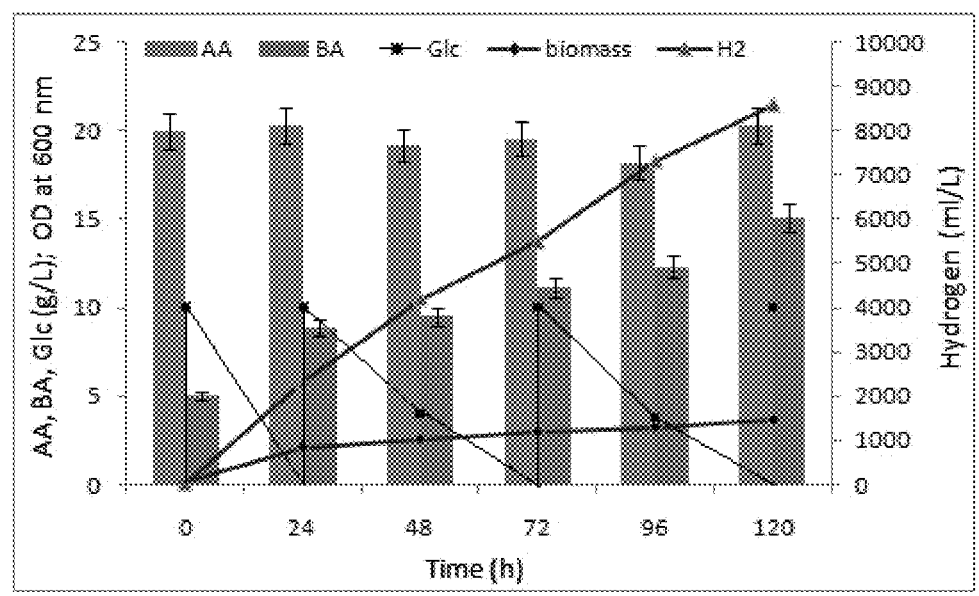
FIG. 2 describes the effect of absence of lactic acid (LA) on $H_2$ production in production media by *Clostridium* sp. IODB-O3 containing 4:1 initial ratio of acetic acid (AA) and butyric acid (BA).

Results and Discussion:

Referring to FIG. 2, higher acetic acid (20 g/L) and lower butyric acid (5 g/L) concentrations did not exhibit enhancement of biohydrogen yield. This experiment was similar to that of the experiment given in example 1, except lactic acid which was lacking here. The yield obtained was maximum 2.57 mol-$H_2$/mol-glucose which was a normal yield range obtained by the culture from glucose substrate in previous studies. The absence of lactic acid was apparent in the experiment which did not improve biohydrogen yield.

FIG. 2 depicts that the hydrogen production rate of the anaerobic fermentative hydrogen production system was not significantly enhanced from the beginning in every 24 h gas volume measurement (two step measurement process in 48 h) in absence of lactic acid. The production of gas volume has been significantly reduced as compared to the production volume. It is assumed that the absence of lactic acid keeps the lactose dehydrogenase functional for lactate production and only higher acetic acid concentration might have inhibited the related genes for acetic acid production such as phosphotransacetylase and acetate kinase and that is also apparent by no increment in acetic acid level as the fermentation progresses. It might have not improved the NAD(P)H level in the pathway, however inhibition of above genes in over all process could not offer any improvement in biohydrogen production.

TABLE 4

Results for FIG. 2

| Time (h) | AA (g/L) | BA (g/L) | $H_2$ (ml/L) | Glucose (g/L) | Biomass (g/L) |
|---|---|---|---|---|---|
| 0 | 20 | 5 | 0 | 10 | 0.1 |
| 24 | 20.3 | 8.9 | 2310 | 10 | 2.09 |
| 48 | 19.2 | 9.5 | 4200 | 3.9 | 2.55 |
| 72 | 19.6 | 11.15 | 5492 | 10 | 2.94 |
| 96 | 18.23 | 12.3 | 7312 | 3.7 | 3.23 |
| 120 | 20.3 | 15.1 | 8582 | 10 | 3.64 |

Example 3

The Effect of Lactic Acid with Inverse Ratio of Acetic and Butyric Acid Supplementation in the Biohydrogen Production Media on Enhancement of Anaerobic Biohydrogen Production This example shows the effect of organic acids with lactic acid addition in biohydrogen production media comprising of glucose as a substrate with growth components along with inverse ratio of acetic and butyric acid supplementation for the anaerobic fermentative biohydrogen production process.

This embodiment investigates the effect of lactic acid addition in production media of *Clostridium* sp IODB-O3 for the production of biohydrogen, however acetic acid and butyric acid were used in inverse concentration ratio as given in example 1. Production media was mainly comprising of glucose as a substrate with all growth components pH indicator, reducing agents and also supplemented with higher concentration of acetic acid (5 g/L w/v) and butyric acid (20 g/L w/v) with lactic acid (3 g/L w/v) as inducer for enhancement of biohydrogen production. The medium pH, incubation temperature, time and agitation were 8.5, 37° C., 48 h, 120 rpm respectively.

Results and Discussion:

In this experiment, higher butyric acid and lower acetic acid concentrations in presence of lactic acid exhibited enhancement of biohydrogen yield but less than that of the experiment discussed in example 1. Please refer to FIG. 3. The yield maximum yield obtained 3.25 mol-$H_2$/mol-glucose and in subsequent cycle, yield was 3.02 mol-$H_2$/mol-glucose. The above yield was also better than the yield obtained by this bacterial strain in normal fermentation condition reported in article Patel et al., 2013.

Figure 3:
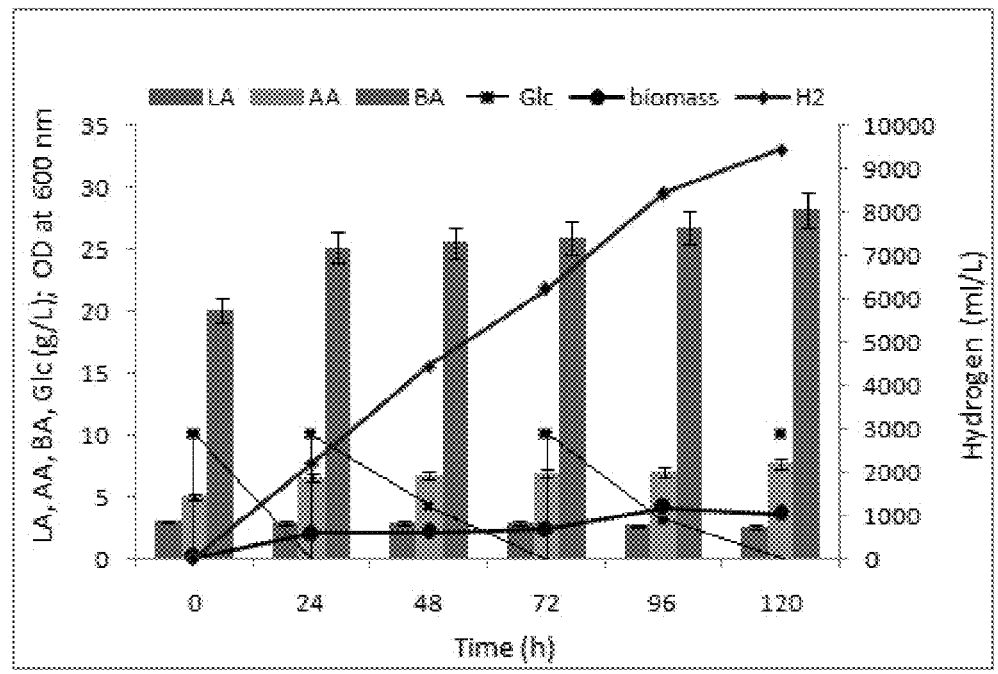
FIG. 3 describes the Biohydrogen production with lactic acid in production media containing 1:4 initial ratio of acetic acid (AA) and butyric acid (BA) concentrations by *Clostridium* sp. IODB-O3.

Referring to FIG. 3, the hydrogen yield of the anaerobic fermentative hydrogen production system was significantly enhanced in every 24 h gas volume measurement (two step measurement process in 48 h) in presence of lactic acid. The production of gas volume has been increased but not as the production volume. It was assumed that the presence of lactic acid inhibited the lactose dehydrogenase for lactate production and higher acetic acid concentration (less concentration as in example 1) might have inhibited the related genes for acetic acid production such as phosphotransacetylase and acetate kinase that is also apparent by no increment in acetic acid level as the fermentation progresses. However, inhibition of above genes in over all process offered little improvement in biohydrogen production but less than the ratio examined in example 1. The yield 3.25 mol-$H_2$/mol-glucose was obtained with 3 g/L lactic acid supplementation in 5 g/L acetic acid and 20 g/L butyric acid containing biohydrogen medium. Based on the performance of IODB-O3 strain in presence of lactic acid in this experiment, the biohydrogen yield was improved by maximum 24.5% as compared to normal fermentation condition without lactic acid supplementation in the media.

TABLE 5

Results for FIG. 3

| Time (h) | LA (g/L) | AA (g/L) | BA (g/L) | $H_2$ (ml/L) | Glucose (g/L) | Biomass (g/L) |
|---|---|---|---|---|---|---|
| 0 | 3 | 5 | 20 | 0 | 10 | 0.1 |
| 24 | 2.9 | 6.6 | 25.1 | 2200 | 10 | 1.99 |
| 48 | 2.92 | 6.8 | 25.5 | 4489 | 4.2 | 2.09 |
| 72 | 2.9 | 6.9 | 25.9 | 6281 | 10 | 2.34 |
| 96 | 2.68 | 7 | 26.7 | 8488 | 3 | 4.1 |
| 120 | 2.53 | 7.7 | 28.2 | 9492 | 10 | 3.64 |

One point is noticeable herein that butyrate production could not be inhibited with any range of external butyric acid addition in all experiments. It was continuously produced in the same production rate by the IODB-O3 strain without being affected by added fraction. The overall yield was improved, may be due to feed-back inhibition of involved enzymes in the pathway by added fraction of lactic acid and acetic acid for the production of the same.

Figure 4:
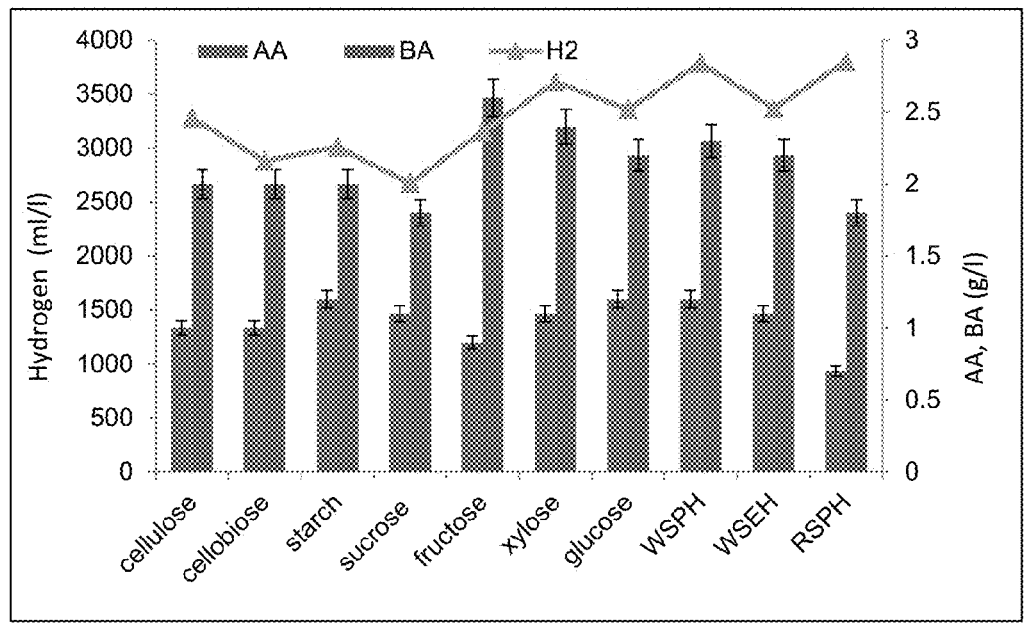
FIG. 4 shows $H_2$ and VFA production profile by utilizing various sugars.

*Clostridium* IODB-O3 has shown $H_2$ and VFA production profile by utilizing various sugars shown in Table 6 below. Lactic acid is not considered as VFA and is not produced by this strain. VFA production (mainly acetic and butyric acid) was obtained more with fructose and xylose (up to 2.4-2.6 g/L BA and 1.0-1.2 g/L AA) followed by WSPH, glucose and WSEH, (FIG. 4).

TABLE 6

VFA and $H_2$ yields with different sugars

| Carbon source or sugar source | Acetic acid (g/L) | butyric acid (g/L) | Yield of $H_2$ (Mol/mol of sugar) |
|---|---|---|---|
| cellulose | 1 | 2 | 2.4 |
| cellobiose | 1 | 2 | 4.4 |
| starch | 1.2 | 2 | 2.2 |
| sucrose | 1.1 | 1.8 | 4.0 |
| fructose | 0.9 | 2.6 | 2.4 |
| xylose | 1.1 | 2.4 | 2.43 |
| glucose | 1.2 | 2.2 | 2.52 |
| WSPH | 1.2 | 2.3 | 2.54 |
| WSEH | 1.1 | 2.2 | 2.65 |
| RSPH | 0.7 | 1.8 | 1.10 |

Some of the Advantages of the Modules of the Present Invention are as Follows:

1. The supplementation of acetic acid and lactic acid will not be required externally in the media. Both fractions will be present in the waste stream and only butyric acid is required to be added, that too only initially.
2) Externally 0.2-0.5% butyric acid is needed to begin the process and once the cell biomass attains 0.2-0.3% concentration, butyric acid can be produced in the required quantity by microbes itself for the rest of the process.
3) Since acetic acid and butyric acid are not consumed in the process, after completion of fermentation, the culture broth can be recycled to recover water, acetic acid and butyric acid fractions, and reuse them to economize the process. The acetic acid is also available commercially, hence it can be added additionally in whey waste to begin the process, and thereafter, it can be recycled and reused.

4) All the three required organic fractions will not be needed regularly to be externally added, which can otherwise be an economic constrain for the process. All these fractions will be fulfilled from waste stream and employed microbes once the process begins and stabilizes. This formulation exhibited maximum percent increase in $H_2$ yield from biological route reported till date. The process will be sustainable and economically viable since it will utilize waste material. This sustainable and cost effective process can remove economic constrains of large scale biohydrogen production process.

5) The existing typical batch process can be modified with proposed new formulation in organic based production media using unique organic acids concentrations for enhancement of anaerobic biohydrogen production, thereby reducing the installation and operational costs.

REFERENCES

1. Baghchehsaraee, B., Nakhla, G., Karamanev, D., Margaritis, A., Reid, G., 2008. The effect of heat pretreatment temperature on fermentative hydrogen production using mixed cultures. Int. J. Hydrogen Energy 33, 4064-4073.
2. Chong, M. L., Rahim, R. A., Shirai, Y., Hassan, M. A., 2009. Biohydrogen production by Clostridium butyricum EB6 from palm oil mill effluent, Int. J. Hydrogen Energy 34, 764-771.
3. deVrije, T., Budde, M. A., Lips, S. J., Bakker, R. R., Mars A. E., Claassen, P. A., 2010. Hydrogen production from carrot pulp by the extreme thermophiles Caldicellulosiruptorsaccharolyticus and Thermotoganeapolitana. Int. J. Hydrogen Energy 35(24), 13206-13213.
4. Hallenbeck, P. C., Benemann, J. R., 2002. Biological hydrogen production; fundamentals and limiting processes. Int. J. Hydrogen Energy 27, 1185-1193.
5. Juang, C. P., Whang, L. M., Cheng, H. H., 2011. Evaluation of bioenergy recovery process treating organic residues from ethanol fermentation process. Bioresour. Technol. 102, 5394-5399.
6. Kamalaskar, B. L., Dhakephalkar, P. K., Meher, K. K., Ranade, D. R., 2010. High biohydrogen yielding Clostridium sp. DMHC-10 isolated from sludge of distillery waste treatment plant. Int. J. Hydrogen Energy 35, 10639-10644.
7. Kim, T H, Lee, Y., Chang, K. H., Hwang, S. J., 2012. Effects of initial lactic acid concentration, HRTs and OLRs on bio-hydrogen production from lactate-type fermentation. Bioresour. Technol. 103, 136-141.
8. Levin, D. B., Pitt, L., Love, M., 2004. Biohydrogen production: prospects and limitation to practical application. Int. J. Hydrogen Energy 29, 173-185.
9. Mars, A. E., Veuskens, T., Budde, M. A., Van Doeveren, P. F. N. M., Lips, S. J., Bakker, R. R., de Vrije, T., Claassen, P. A., 2010. Biohydrogen production from untreated and hydrolyzed potato steam peels by the extreme thermophiles Caldicellulosiruptorsaccharolyticus and Thermotoganeapolitana. Int. J. Hydrogen Energy 35, 7730-7737.
10. Masumoto, M., Nishimura, Y., 2007. Hydrogen production by fermentation using acetic acid and lactic acid. J. Biosci. Bioeng. 103, 236-241.
11. Munro, S. A., Zinder, S. H., Wlaker, L. P., 2009. The fermentation stoichiometry of Thermotoganeapolitana and influence of temperature, oxygen and pH on hydrogen production. Biotech. Progress 25 (4) 1035-1042.
12. Ngo, T. A., Nguyen, T. H., Bui, H. T. V., 2012. Thermophilic fermentative hydrogen production from xylose by Thermotoganeopolitana DSM 4359. Renewable Energ. 37 (1), 174-179.
13. Noike, T., Takabatake, H., Mizuno, O., Ohba, M., 2002. Inhibition of hydrogen fermentation of organic wastes by lactic acid bacteria. Int. J. Hydrogen Energy 27, 1367-1371.
14. Oh, Y. K., Kim, H. J., Park, S., Kim, M. S., Ryu, D. D. Y., 2008. Metabolic-flux analysis of hydrogen production pathway in Citrobacteramalonaticus Y19. Int. J. Hydrogen Energy 33, 1471-1482.
15. Patel, A. K., Debroy, A., Sharma, S., Saini, R., Mathur, A., Gupta, R., Tuli, D. K., 2015. Biohydrogenproduction from a novel alkalophilic isolate Clostridium sp. IODB-O3, Bioresour. Technol. 175, 291-297.
16. Woodward, J., Orr, M., Cordray, K., Greenbaum, E., 2000. Biotechnology: Enzymatic production of biohydrogen. Nature 405, 1014-1015.
17. Hungate, R. E., 1969. A roll tube method for cultivation of strict anaerobes. Methods Microbiol. 33, 117-132.
18. Singh, S., Sudhakaran, A. K., Sarma, P. M., Subudhi, S., Mandal, A. K., Gandham, G., Lal, B., 2010. Dark fermentative biohydrogen production by mesophilic bacterial consortia isolated from riverbed sediments. Int. J. Hydrogen Energ. 35, 10645-10652.
19. Wu, C. W., Whang, L. M., Cheng, H. H., Chan, K. C., 2012. Fermentative biohydrogen production from lactate and acetate, Bioresour. Technol 113, 30-36.

The invention claimed is:

1. A process for enhancing hydrogen production in an anaerobic fermentative hydrogen production process, the process comprising:
   providing a production medium,
   incubating the production media with an anaerobic Clostridium sp. at 37° C. and pH 8.5 for anaerobic fermentative reaction to produce hydrogen,
   wherein the process comprises supplementing the production medium with lactic acid, acetic acid and butyric acid,
   wherein the ratio of acetic acid and butyric acid before the incubating step is 4:1.

2. The process of claim 1, wherein the production media is a sugar based production media.

3. The process of claim 2, wherein the sugar is selected from glucose, lactose, xylose, wheat straw pre-hydrolysate (WSPH) and wheat straw enzymatic-hydrolysate (WSEH).

4. The process of claim 1, wherein the Clostridium sp. is Clostridium sp., MTCC 25082.

5. The process of claim 1, wherein the amount of lactic acid in the production medium is about 0.3% w/v, the amount of acetic acid is about 2% w/v, and the amount of butyric acid is about 0.5% w/v.

6. The process of claim 1, wherein acetic acid and butyric acid fractions are recovered from the production medium after the incubating step and are recycled.

7. The process of claim 1, wherein the amount of hydrogen production is 3.5 to 4.5 mol/mol-sugar.

* * * * *